United States Patent [19]

Luster

[11] Patent Number: 5,715,051
[45] Date of Patent: Feb. 3, 1998

[54] METHOD AND SYSTEM FOR DETECTING DEFECTS IN OPTICALLY TRANSMISSIVE COATINGS FORMED ON OPTICAL MEDIA SUBSTRATES

[75] Inventor: Spencer D. Luster, Toledo, Ohio

[73] Assignee: Medar, Inc., Farmington Hills, Mich.

[21] Appl. No.: 735,197

[22] Filed: Oct. 21, 1996

[51] Int. Cl.$^6$ ............................................. G01N 21/00
[52] U.S. Cl. ............................ 356/239; 356/237; 356/71
[58] Field of Search ................................ 356/239, 237, 356/71

[56] References Cited

U.S. PATENT DOCUMENTS

| | | | |
|---|---|---|---|
| 4,568,984 | 2/1986 | Juergensen et al. | 356/239 |
| 5,067,812 | 11/1991 | Sugimura et al. | 356/239 |
| 5,268,735 | 12/1993 | Hayashi | 356/239 |

*Primary Examiner*—Frank G. Font
*Assistant Examiner*—Reginald A. Ratliff
*Attorney, Agent, or Firm*—Brooks & Kushman P.C.

[57] ABSTRACT

Spectral transmittance of a dye coating for optical data is determined off-line. Light source wavelength is then matched to the wavelengths at which the dye has the least transmission (i.e. maximum absorbance). The method and system of the present invention are provided for detecting local and global defects in the coating wherein the inspection is done at the maximum absorbance wavelengths to produce a maximum change in a transmitted light signal for a given change in physical thickness of the dye coating. Relative change in thickness is determined based on the change in the transmitted light signal through the dye coating. In order to complete detection and measurement of the transmittance changes, a pair of electronic signals are split from a camera signal wherein one of the electronic signals is filtered by a FIR filter to identify local changes in dye thickness against a globally varying background. In order to detect global variations in the dye thickness, the other electronic signal is processed by a simple thresholding circuit.

24 Claims, 3 Drawing Sheets

METHOD AND SYSTEM FOR DETECTING DEFECTS IN OPTICALLY TRANSMISSIVE COATINGS FORMED ON OPTICAL MEDIA SUBSTRATES

TECHNICAL FIELD

This invention generally relates to optically-based, automated disk inspection and, in particular, to methods and systems for detecting defects in optically transmissive coatings formed on optical media substrates.

BACKGROUND ART

Compact Disk Recordable format (CD-R) is an optical data storage technology that relies in part on specialized dye coatings. These coatings are generally applied to clear substrates, typically polycarbonate. An additional metal coating, usually gold, is applied on top of the dye, followed by a protective lacquer.

During the writing process, a modulated laser induces local physical changes in the dye which remain as the data to be recorded and later read. Proper dye composition, thickness, and uniformity is critical for proper functioning. A strong indicator of good overall dye function is the percent transmittance of light (at the operating wavelength) through the dye and substrate. The range of acceptable transmittance will depend on the particular dye and process.

It is desirable to detect relative changes in the thickness of dye coatings used on CD-R substrates on-line at production speeds. This is useful not only for the detection of localized defects in order to maintain disk writeability/readability, but also to insure not too much or too little dye is laid down globally. Both cases can impair disk function. Also, the dyes used for CD-R are generally expensive and excess dye might be deemed an unacceptable waste.

Current optically-based, automated disk inspection technology relies in part on spectrally broadband white light or "convenient" laser or light-emitting diode wavelengths. By "convenient", it is meant wavelengths from devices that are readily available. Such wavelengths typically include narrow band sources centered around the wavelengths 880 nm, 830 nm, 780 nm, and 680 nm to 630 nm.

The problem with such wavelengths is that they typically do not match the peak spectral absorbance of the dye. In fact, the dye may have a particularly high transmission at the typical operating wavelength of 780 nm. As a result of having a high transmission (low attenuation coefficient), variations in the dye thickness are not readily detected by observing variations in the amount of light transmitted through the dye. This is a well known physical principle.

Additionally, many prior art inspection systems rely on simple thresholding of opto-electronic signals from detectors or cameras. This process is not suited to CD-R dye inspection, even with proper wavelength selection, because part of the requirement is to detect local (high spatial frequency), low amplitude dye variations against a global (low spatial frequency), low to medium amplitude background dye variation. FIG. 1 shows an example of a prior art system based on a linear array camera 10, a lens 12, a motor and interconnected base (not shown) for rotating a disk 14 in a direction given by an arrow 16, and a non-wavelength-matched light source 18. Even though a dye thickness variation might be significant, as illustrated in FIG. 2, there is little signal differentiation as seen by the camera 10, as illustrated in FIG. 3.

Alternatively, frequency filtering of the signal via full grey scale software processing is probably too slow to keep up with production speeds considering the high resolution (large data volume) requirements of CD-R inspection.

Another method relies on point-at-a-time reading of the disk as it rotates, much in the same way an optical disk reader/player operates. While this method is very high resolution, and is probably capable of detecting the desired variations (those which would affect an actual CD-R writer/reader), it is far too slow for 100% inspection at production speeds In summary, prior methods of detecting dye coating thickness variations are either insufficiently sensitive or are too slow to keep up with production speeds. Prior art devices use light sources which are not optimized to detect dye thickness changes (improper matching of maximum dye absorbance with wavelength) or are systems built around pseudo-disk reading devices. Such devices take many minutes to inspect a disk while production rates may be less than 5 seconds per disk.

SUMMARY OF THE INVENTION

An object of the present invention is to provide a method and system for detecting defects in an optically transmissive coating formed on an optical media substrate by illuminating the coating with light having a wavelength matched with peak absorption wavelengths of the coating.

Another object of the present invention is to provide a method and system for detecting defects in an optically transmissive coating formed on an optical media substrate on-line and at production speeds.

Still another object of the present invention is to provide a method and system for detecting relative thickness changes of dye coatings used on CD-R substrates on-line and at production speeds.

Yet still another object of the present invention is to provide a method and system for detecting local and global defects in an optically transmissive coating formed on an optical media substrate.

In carrying out the above objects and other objects of the present invention, a method is provided for detecting defects in an optically transmissive coating formed on an optical media substrate. The method includes the step of illuminating the coating with light having a wavelength matched to the peak absorption wavelengths of the coating to obtain a transmitted light signal. The method also includes the step of generating a first electronic signal from the transmitted light signal. The first electronic signal has high frequency defect data and background data having a frequency less than the frequency of the high frequency defect data. The method finally includes the step of processing at least the high frequency defect data to determine defects in real-time.

Preferably, the method also includes the step of filtering the first electronic signal to pass the high frequency defect data while substantially eliminating the background data and wherein the step of processing the at least high frequency defect data determines local defects in real-time.

Also, preferably, the method includes the step of generating a second electronic signal having the high frequency defect data and the background data and processing high frequency defect data and the background data to determine global defects in real-time.

Still preferably, the coating is a dye coating and the optical media substrate is an optical disk.

Further in carrying out the above objects and other objects of the present invention, a system is provided for carrying out the above method steps.

The advantages accruing to method and system of the present invention are numerous. For example, (1) variations in dye thickness are readily detected by observing variations in the amount of light transmitted through the dye; this is due to matching of illumination wavelength with the peak absorption wavelengths of the dye coating; (2) hardware based selectable frequency filtering allows for the separate detection of local defects (high spatial frequency) as well as global defects (low spatial frequency or large area dye thickness variations); and (3) splitting of the camera signal into a filtered and unfiltered channels allows simultaneous detection of local defects as well as unacceptable global variations at high speed.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

In general, the method and system of the present invention includes three features as follows:

1. The spectral transmittance of the dye is determined off-line via standard methods. Important results are the transmittance at the disk operating wavelength as well as the wavelengths of least transmission. This information allows for the calculation of the attenuation coefficients of the dye for these wavelengths. This is a standard, well known calculation.

Figure 1:
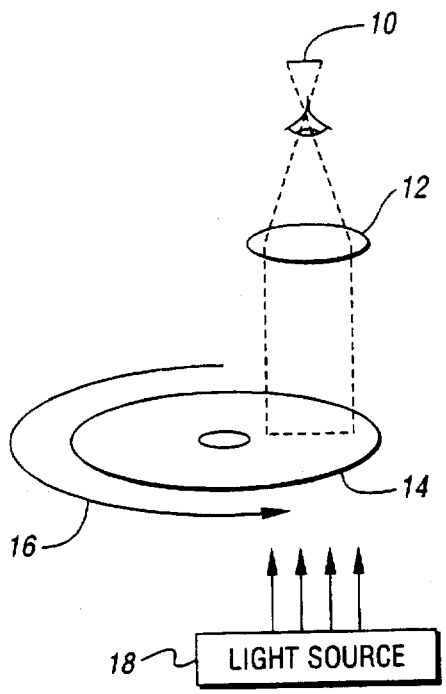
FIG. 1 is a schematic diagram illustrating a prior art method and system.
Figure 2:
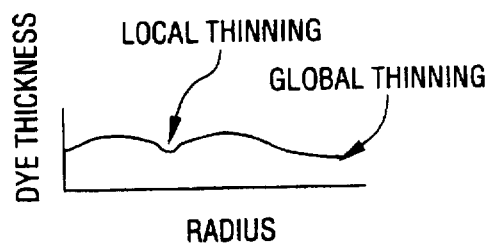
FIG. 2 is a graph illustrating dye thickness variation on an optical media substrate.
Figure 3:
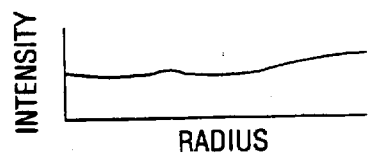
FIG. 3 is a graph illustrating little signal variation from the camera of FIG. 1 for the dye thickness variation of FIG. 2.
Figure 4:
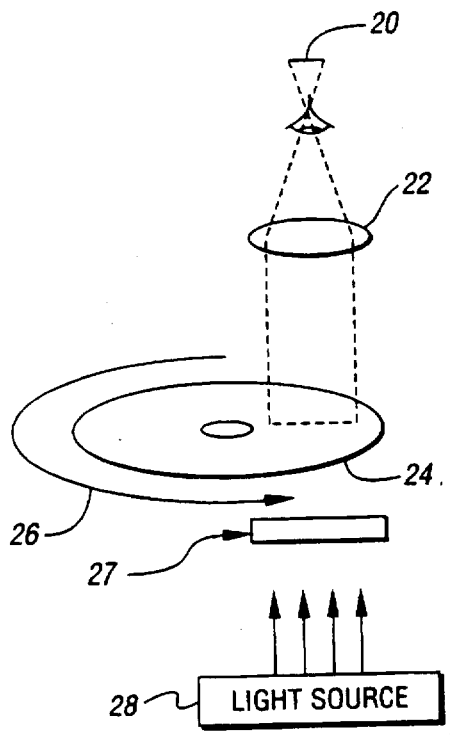
FIG. 4 is a schematic diagram similar to the diagram of FIG. 1, but illustrating the method and system of the present invention.
Figure 5:
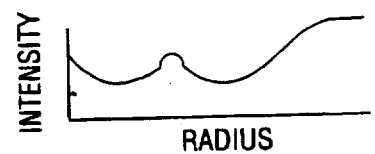
FIG. 5 is a graph similar to FIG. 3, but now illustrating strong differentiation of signals from the camera of FIG. 4 due to the dye thickness variations of FIG. 2.

The on-line inspection system light source wavelength is designed to match the wavelengths for which the dye has the least transmission—maximum absorbance. Inspection at the maximum absorbance wavelengths will produce the maximum change in signal for a given change in physical thickness of the dye illustrated in FIG. 2. FIG. 5 shows such an effect for a system of the present invention as illustrated in FIG. 4. The system includes a linear array camera 20, a lens 22, means for rotating a disk 24 in a direction given by an arrow 26, a spectral filter 27 to match dye absorbance, and a light source 28.

Assuming the dye material is homogeneous, or at least that inhomogeneities are randomly distributed through the volume of material, the relative change in thickness can be determined based on the change in signal. From this point, the change in transmittance at the operating wavelength can then be calculated. This process can be more accurate than direct measurement of the relatively small change in transmittance at the operating wavelength because of the increased signal-to-noise ratio.

Figure 6:
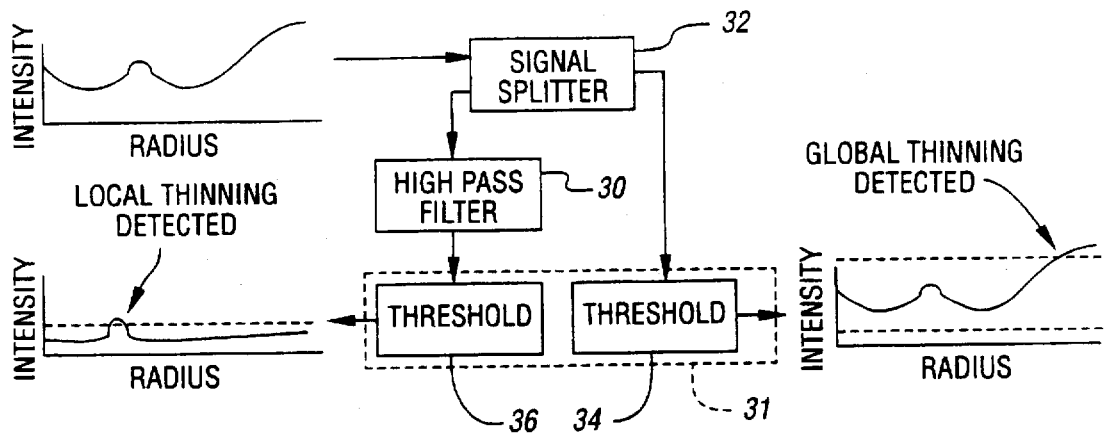
FIG. 6 is a schematic diagram, including graphs, illustrating a portion of the method and system of the present invention.

2. Given that the proper choice of wavelength allows for detection and measurement of transmittance changes at all, the next step is to properly filter the signals and identify the local changes against a globally varying background. Again, this in itself is a standard technique, assuming there is a frequency difference between the signals, but doing it at production speeds can be difficult. In order to accommodate the high speed filtering required, in-line hardware high pass filtering was developed. In the tested implementation, a Finite Impulse Response (FIR) filter 30 is used as illustrated in FIGS. 6 and 7.

3. In addition to the local defects, it is desired to detect global variations or defects that exceed certain limits. This information, however, is essentially lost upon high pass filtering. By the technique of splitting the camera output signal, illustrated by the graph on the upper left hand side of FIG. 6, into two parallel channels, filtered and unfiltered, by a signal splitter 32 of FIGS. 6 and 7, both local and global variations may be detected, the latter by a simple thresholding technique by a threshold circuit 34 of an image processing band 31. The graph on the right hand side of FIG. 6 illustrates detection of global thinning.

Local variations are detected by a separate threshold circuit 36 of the image processing band 31. The graph on the lower left hand side of FIG. 6 illustrates detection of local thinning.

Figure 7:
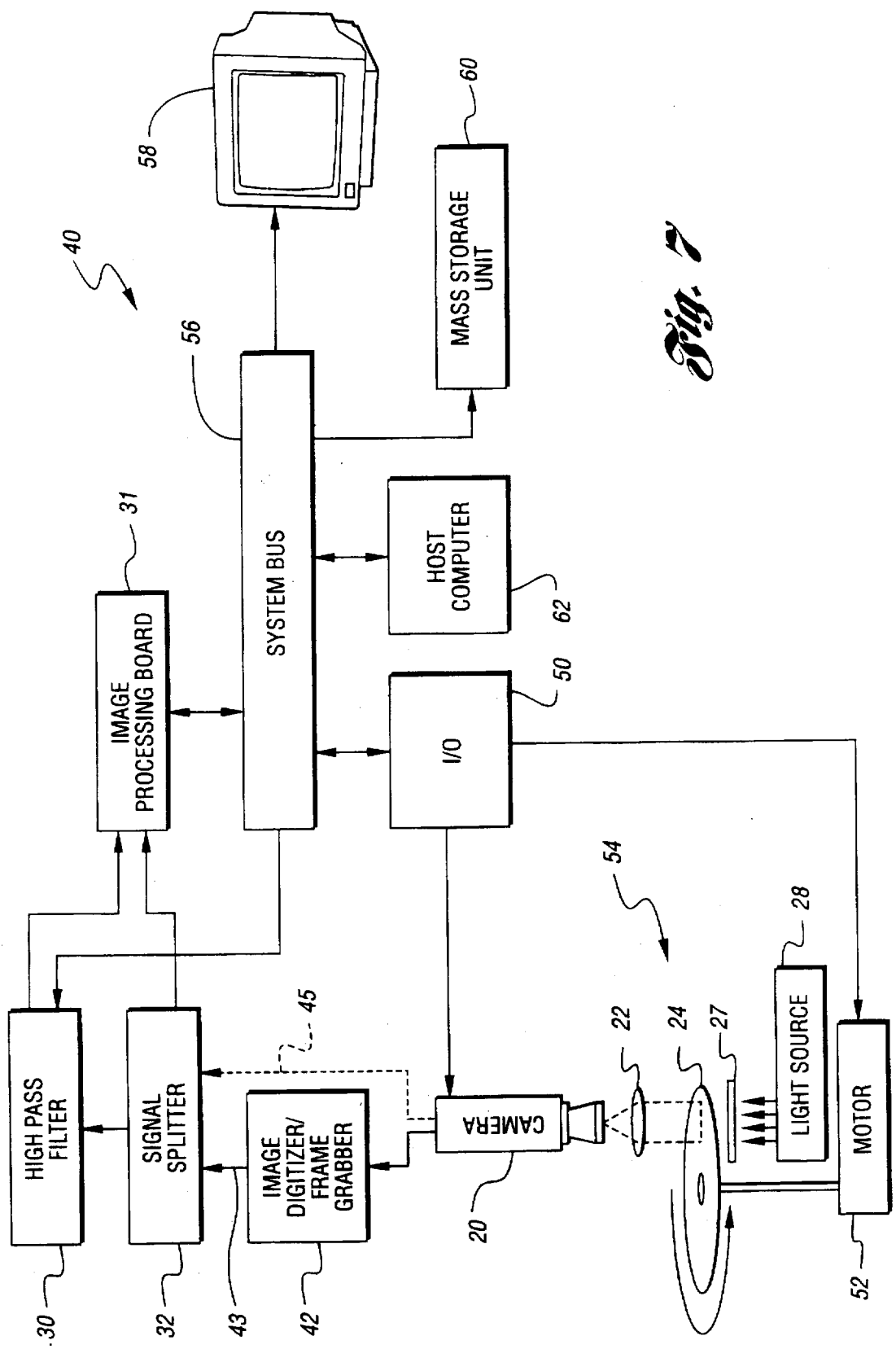
FIG. 7 is a schematic block diagram illustrating a machine vision system for carrying out the present invention.

Referring specifically to FIG. 7, there is illustrated schematically a machine vision system, generally indicated at 40, by which the method and system of the present invention can reliably detect local and global defects in an optically transmissive dye coating formed on an optical media substrate. Preferably, the method and system use digital filtering techniques to detect the localized defects in the dye after application on the substrate. The substrate may be an optical media substrate such as an optical or CD-R disk 24.

The machine vision system 40 typically includes an image digitizer/frame grabber 42. The image digitizer/frame grabber 42 samples and digitizes input images from the camera 20 along line 43 and places each input image into a frame buffer having picture elements. The image/digitizer/frame grabber 42 may be a conventional frame grabber board such as that manufactured by Matrox, Cognex, Data Translation or other frame grabbers. Alternatively, the image digitizer/frame grabber 42 may comprise a vision processor board such as made by Cognex.

Each of the picture elements may consist of an 8-bit number representing the brightness of that spot in the image. If the camera 30 is a digital camera, the digital camera will eliminate the need for the image digitizer/frame grabber 42 and the input image appears along a line 45.

The system 40 also includes input/output circuits 50 to allow the system 40 to communicate with external devices such as a controller (not shown) for controlling a motor such as a stepper motor 52. The disk 24 is rotatably mounted on a base at a free end of an output shaft of the motor 52 at an inspection station 54. Typically, the camera 20 scans radially extending portions of the disk 24 as it rotates, as illustrated in FIG. 4.

The I/O circuits 50 also allow the system 40 to communicate with a controller (not shown) for controlling the camera 20 at the inspection station 54. The camera 20 may be an image source such as an analog, digital or linear array and is preferably a linear array camera.

The inspection station 54 also includes the light source 28 such as a projection lamp with the filter 27 between the light source 28 and the rotating disk 24, as illustrated in FIG. 4.

The machine vision system 40 also includes a system bus 56 which may be either a PCI, an EISA, ISA or VL system bus or any other standard bus to allow inter-system communication such as with a monitor 58 of the system 40, the image processing board 31, and the high pass filter 30.

The machine vision system 40 may be programmed at a mass storage unit 60 to include custom controls for image processing and image analysis.

A host computer 62 of the system 40 may be a PC having a sufficient amount of RAM and hard disk space for computer programs for controlling the system 40.

Figure 8:
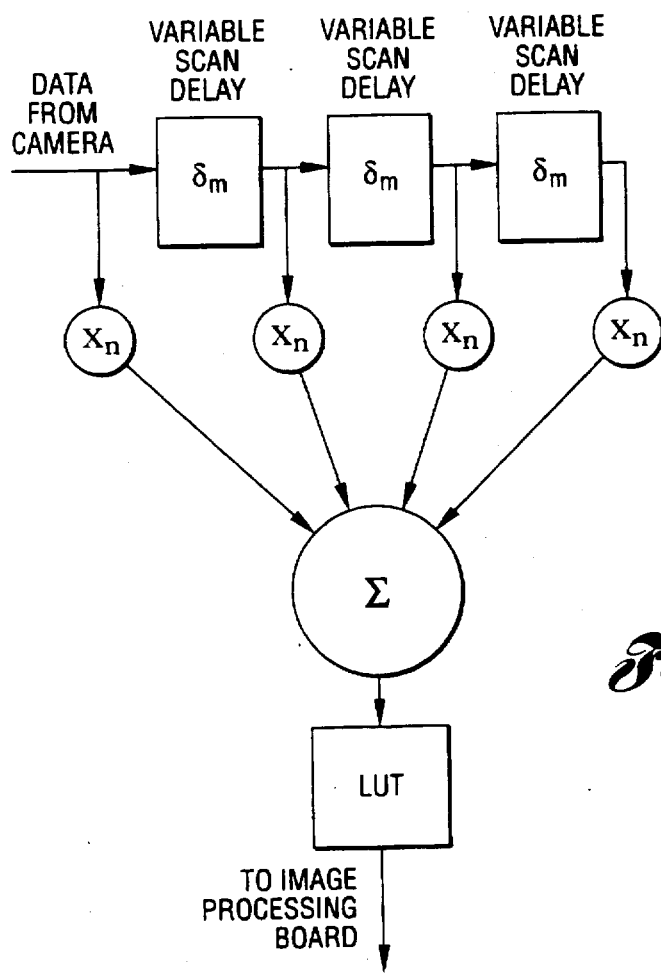
FIG. 8 is a schematic block diagram of the high pass filter of the present invention.

The digital filter 30 preferably comprises a finite impulse response (FIR) filter which comprises a scan-to-scan filter, as illustrated in FIG. 8. The scan-to-scan filter implements a four stage impulse response (FIR) filter in the scanning direction. The inputs to latches of the filter are the same pixel locations in different scans. For each new pixel, the following takes place: 1) shift out old pixel; 2) multiply each of the four pixels by their individual constants; 3) sum output of multiplication; and 4) adjust output with a look-up-table (i.e., LUT).

Each of the four stages has its own multiplier. The constant in each multiplier can range from 1 to −1 in $1/512$ increments and is programmable. The result of the summer stage is represented in 23 bits. The most significant ten bits are used as the address to the look-up-table memory (also programmable). This memory can transform negative output values to positive values for use by the image processing board 31. The software on the host computer 62 typically initializes all the constants (i.e. filter coefficients) and the look-up-table memory. Preferably, the filter 30 includes four (4) pipelined registered multipliers followed by a summer and an accumulator. Still, preferably, the filter 30 is implemented using a Raytheon semiconductor integrated circuit having the designation TMC 2246 CMOS Image Filter.

The output data of the filter 30 is typically post-processed at a data squelch circuit (not shown) to accomplish gain and offset correction, as well as impose nonlinear characteristics on the output data if desired. These nonlinear characteristics can be used to implement a data squelch.

In summary, the digital filter 30 allows the detection of local defects and the real-time data rate of the filter 30 has a large advantage over pure software methods. In other words, the filter 30 passes the high frequency defects through to the camera processing board 31 while eliminating the not quite so high frequency background from its input signal. The reason for using the digital filter 30 instead of a high pass filter is that the frequency difference between the background and the defect data is small and the processing needs to be done in real-time (10 MHz pixel rate).

While the best mode for carrying out the invention has been described in detail, those familiar with the art to which this invention relates will recognize various alternative designs and embodiments for practicing the invention as defined by the following claims.

What is claimed is:

1. A method for detecting defects in an optically transmissive coating formed on an optical media substrate, the method comprising the steps of:

illuminating the coating with light having a wavelength matched to peak absorption wavelengths of the coating to obtain a transmitted light signal;

generating a first electronic signal from the transmitted light signal, the first electronic signal having high frequency defect data and background data having a frequency less than the frequency of the high frequency defect data;

filtering the first electronic signal to pass the high frequency defect data while substantially eliminating the background data; and processing at least the high frequency defect data to determine the defects in real-time wherein the step of processing determines local defects in real-time.

2. The method as claimed in claim 1 wherein the coating is a dye coating.

3. The method as claimed in claim 1 wherein the optical media substrate is an optical disk.

4. The method as claimed in claim 3 wherein the optical disk is a recordable, compact disk.

5. The method as claimed in claim 1 wherein the optical media substrate is substantially transparent.

6. The method as claimed in claim 1 wherein the step of filtering is accomplished digitally.

7. The method as claimed in claim 1 wherein the first electronic signal includes a data stream of image data wherein the high frequency defect data is based on present and previous sample values of the data stream of image data.

8. A method for detecting defects in an optically transmissive coating formed on an optical media substrate, the method comprising the steps of:

illuminating the coating with light having a wavelength matched to peak absorption wavelengths of the coating to obtain a transmitted light signal;

generating a first electronic signal from the transmitted light signal, the first electronic signal having high frequency defect data and background data having a frequency less than the frequency of the high frequency defect data;

generating a second electronic signal having the high frequency defect data and background data, and processing at least the high frequency defect data to determine the defect in real time wherein the step of processing includes the step of processing the high frequency defect data and the background data to detect global defects in real-time.

9. The method as claimed in claim 8 wherein the step of processing the high frequency defect data and the background data includes the step of thresholding the high frequency defect data and the background data.

10. A system for detecting defects in an optically transmissive coating formed on an optical media substrate, the system comprising:

a base for supporting the optical media substrate with an optical transmissive coating formed thereon;

means for illuminating the coating with light having a wavelength matched to peak absorption wavelengths of the coating to obtain a transmitted light signal;

means for generating a first electronic signal from the transmitted light signal, the first electronic signal having high frequency defect data and background data having a frequency less than the frequency of the high frequency defect data;

a filter for filtering the first electronic signal to pass the high frequency defect data while substantially eliminating the background data; and a processor for processing at least the high frequency defect data to determine the defects in real-time wherein the processor processes the high frequency defect data to determine local defects in real-time.

11. The system as claimed in claim 10 wherein the coating is a dye coating.

12. The system as claimed in claim 10 wherein the optical media substrate is an optical disk.

13. The system as claimed in claim 12 wherein the optical disk is a recordable, compact disk.

14. The system as claimed in claim 10 wherein the optical media substrate is substantially transparent.

15. The system as claimed in claim 10 wherein the filter is a finite impulse response filter.

16. The system as claimed in claim 10 wherein the filter is a digital filter.

17. The system of claim 12 wherein the means for illuminating includes a light source for generating light and a spectral filter for spectrally filtering the generated light to pass the light having the wavelength matched to the peak absorption wavelengths of the coating.

18. A system for detecting defects in an optically transmissive coating formed on an optical media substrate, the system comprising:

a base for supporting the optical media substrate with an optical transmissive coating formed thereon;

means for illuminating the coating with light having a wavelength matched to peak absorption wavelengths of the coating to obtain a transmitted light signal;

means for generating a first electronic signal from the transmitted light signal, the first electronic signal having high frequency defect data and background data having a frequency less than the frequency of the high frequency defect data wherein the means for generating includes a camera adapted to respond to the transmitted light signal to obtain a camera signal;

a splitter for splitting the camera signal into the first electronic signal and a second electronic signal, the second electronic signal also having the high frequency defect data and the background data; and a processor for processing at least the high frequency defect data to determine the defects in real-time.

19. The system of claim 18 wherein the processor processes the high frequency defect data and the background data to obtain global defects.

20. The system as claimed in claim 19 wherein the processor includes a thresholding circuit for thresholding the high frequency defect data and the background data to determine the global defects.

21. The system of claim 20 further comprising a computer coupled to the camera for controllably operating the camera.

22. The system of claim 21 further comprising a motor adapted to move the base in response to a control signal from the computer.

23. The system of claim 22 wherein the base rotatably supports the optical media substrate and wherein the motor rotates the base in response to the control signal.

24. The system of claim 20 wherein the camera is a linear array camera.

* * * * *